(12) United States Patent
Schaller

(10) Patent No.: US 10,485,261 B2
(45) Date of Patent: Nov. 26, 2019

(54) AEROSOL-GENERATING SYSTEM COMPRISING A NOVEL DELIVERY ENHANCING COMPOUND SOURCE

(71) Applicant: Philip Morris Products S.A., Neuchatel (CH)

(72) Inventor: Jean-Pierre Schaller, Geneva (CH)

(73) Assignee: Philip Morris Products S.A., Neuchatel (CH)

(*) Notice: Subject to any disclaimer, the term of this patent is extended or adjusted under 35 U.S.C. 154(b) by 415 days.

(21) Appl. No.: 15/512,599

(22) PCT Filed: Sep. 25, 2015

(86) PCT No.: PCT/EP2015/072088
§ 371 (c)(1),
(2) Date: Mar. 20, 2017

(87) PCT Pub. No.: WO2016/046362
PCT Pub. Date: Mar. 31, 2016

(65) Prior Publication Data
US 2017/0303581 A1     Oct. 26, 2017

(30) Foreign Application Priority Data

Sep. 26, 2014  (EP) .................................. 14186700

(51) Int. Cl.
*A61M 15/06*     (2006.01)
*A24B 15/16*     (2006.01)
(Continued)

(52) U.S. Cl.
CPC ............ *A24B 15/167* (2016.11); *A24B 15/16* (2013.01); *A24F 47/008* (2013.01); *B65B 29/10* (2013.01);
(Continued)

(58) Field of Classification Search
None
See application file for complete search history.

(56) References Cited

FOREIGN PATENT DOCUMENTS

| CN | 103462211 A | 12/2013 |
|----|-------------|---------|
| CN | 103610229 A | 3/2014  |

(Continued)

OTHER PUBLICATIONS

International Search Report and Written Opinion dated Dec. 4, 2015 in PCT/EP2015/072088, filed Sep. 25, 2015.

(Continued)

*Primary Examiner* — Thor S Campbell
(74) *Attorney, Agent, or Firm* — Oblon, McClelland, Maier & Neustadt, L.L.P.

(57) ABSTRACT

An aerosol-generating system is provided, including a nicotine source; and a delivery enhancing compound source, which includes a reaction product of one or both of:
 (i) an alpha-keto carboxylic acid and a compound of formula (I)

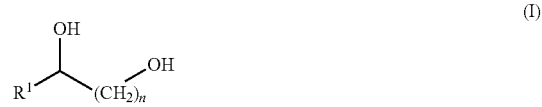

Figure 1:
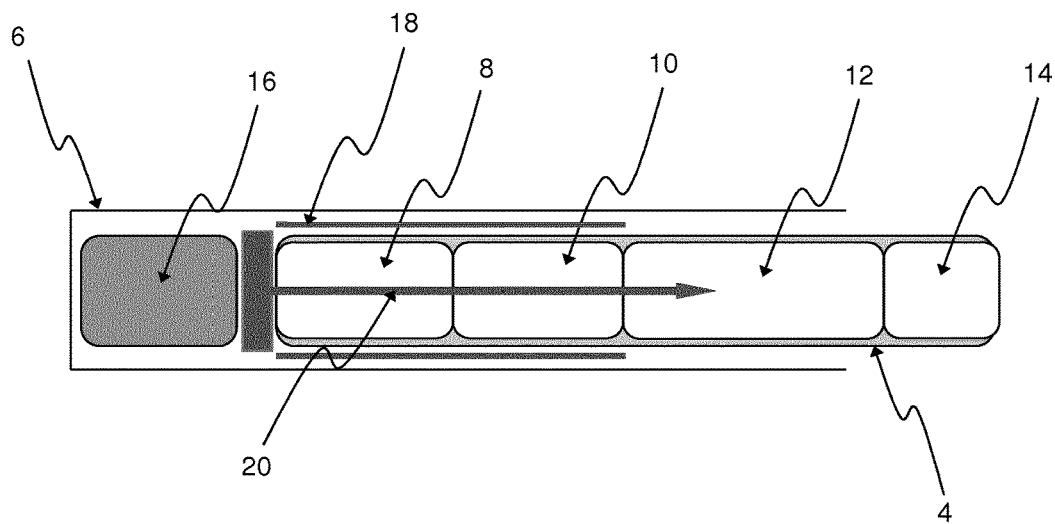

where R¹ is selected from alkyl, phenyl, or substituted phenyl, and
(ii) an alpha-hydroxy acid and a compound of formula (II)

(Continued)

where X is a halogen and $R^2$ is selected from H, alkyl, phenyl, or substituted phenyl.

15 Claims, 1 Drawing Sheet

(51) Int. Cl.
    *B65B 29/10*     (2006.01)
    *A24F 47/00*     (2006.01)
    *C07C 59/60*     (2006.01)
    *C07D 317/32*     (2006.01)
    *C07D 401/04*     (2006.01)

(52) U.S. Cl.
    CPC ............ *C07C 59/60* (2013.01); *C07D 317/32* (2013.01); *C07D 401/04* (2013.01)

(56) References Cited

FOREIGN PATENT DOCUMENTS

| | | | |
|---|---|---|---|
| CN | 103653234 A | 3/2014 | |
| CN | 103653235 A | 3/2014 | |
| CN | 103908014 A | 7/2014 | |
| CN | 103989244 A | 8/2014 | |
| EP | 1 201 142 A1 | 5/2002 | |
| EP | 2 269 475 A1 | 1/2011 | |
| JP | 5-97842 | 4/1993 | |
| WO | WO 2006/002001 A2 | 1/2006 | |
| WO | WO 2006/022784 A1 | 3/2006 | |
| WO | WO 2008/121161 A2 | 10/2008 | |
| WO | WO 2008/121610 A1 | 10/2008 | |
| WO | WO 2013/128176 A1 | 9/2013 | |
| WO | WO 2014/139611 A1 | 9/2014 | |
| WO | WO 2014/140087 A1 | 9/2014 | |
| WO | WO 2014/140320 A1 | 9/2014 | |
| WO | WO 2015/040180 A2 | 3/2015 | |

OTHER PUBLICATIONS

Combined Chinese Office Action and Search Report dated Dec. 29, 2017, in Patent Application No. 201580048088.7 (with English translation), citing documents AM-AV therein, 13 pages.
Robert C. Kerber, et al., "α-Oxocarboxylic Acids", American Chemical Society and Division of Chemical Education, Inc., Journal of Chemical Education, vol. 87, No. 10, Oct. 2010, pp. 1079-1084.
Melvin S. Newman, et al., "The Reaction of Cyclic α-Ketal Acids with Phosphorus Pentachloride. A New Stereospecific Route to Esters of Halohydrins", J. Org. Chem., vol. 38, No. 6, 1973, pp. 1173-1177.
Japanese Office Action with English translation dated Aug. 22, 2019 in corresponding Japanese Patent Application No. 2017-516701, (4 pages).

AEROSOL-GENERATING SYSTEM COMPRISING A NOVEL DELIVERY ENHANCING COMPOUND SOURCE

The present invention relates to an aerosol-generating system comprising a nicotine source and a delivery enhancing compound source. In particular, the present invention relates to an aerosol-generating system comprising a nicotine source and a delivery enhancing compound source for generating an aerosol comprising nicotine salt particles.

Devices for delivering nicotine to a user comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

Differences between the vapour concentrations of nicotine and the volatile delivery enhancing compound in such devices may disadvantageously lead to an unfavorable reaction stoichiometry or the delivery of excess reactant, such as unreacted nicotine vapour or unreacted volatile delivery enhancing compound vapour to a user. The vapour pressure of pyruvic acid at ambient temperature is substantially greater than that of nicotine. Consequently, to balance the concentration of pyruvic acid vapour and nicotine vapour to yield an efficient reaction stoichiometry, it has been proposed to heat the nicotine source and the pyruvic acid source to different temperatures. Specifically, it has been proposed to heat the nicotine source to a higher temperature than the pyruvic acid source in order to generate a sufficient or consistent quantity of nicotine pyruvate salt particles for delivery to a user. This may disadvantageously increase the complexity and cost of manufacturing the device.

It would be desirable to provide an aerosol-generating system comprising a nicotine source and a delivery enhancing compound source for the in situ generation of an aerosol comprising a nicotine salt which system is simple to manufacture and which enables an efficient reaction stoichiometry and consistent nicotine delivery to a user.

It would also be desirable to provide an aerosol-generating system comprising a nicotine source and a delivery enhancing compound source for the in situ generation of an aerosol comprising a nicotine salt in which the delivery enhancing compound is sufficiently stable to be stored for longer periods without substantial polymerization or decomposition, which may disadvantageously alter the properties of the delivery enhancing compound.

According to the present invention there is provided an aerosol-generating system comprising: a nicotine source; and a delivery enhancing compound source, wherein the delivery enhancing compound source comprises the reaction product of one or both of:
(i) an alpha-keto carboxylic acid and a compound of formula (I)

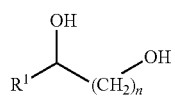

wherein $R^1$ is selected from alkyl, phenyl or substituted phenyl; and
(ii) an alpha-hydroxy acid and a compound of formula (II)

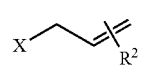

wherein X is halogen and $R^2$ is selected from H, alkyl, phenyl or substituted phenyl.

According to the present invention there is also provided an aerosol-generating system comprising: an aerosol-generating article comprising a nicotine source and a delivery enhancing compound source, wherein the delivery enhancing compound source comprises the reaction product of one or both of:
(i) an alpha-keto carboxylic acid and a compound of formula (I)

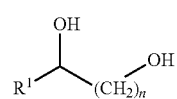

wherein $R^1$ is selected from alkyl, phenyl or substituted phenyl; and
(ii) an alpha-hydroxy acid and a compound of formula (II)

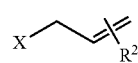

wherein X is halogen and $R^2$ is selected from H, alkyl, phenyl or substituted phenyl; and an aerosol-generating device configured to receive the nicotine source and the delivery enhancing compound source of the aerosol-generating article.

According to the present invention there is also provided an aerosol-generating article for use in an aerosol-generating system according to the present invention, the aerosol-generating article comprising a nicotine source and a delivery enhancing compound source, wherein the delivery enhancing compound source comprises the reaction product of one or both of:
(i) an alpha-keto carboxylic acid and a compound of formula (I)

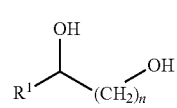

wherein $R^1$ is selected from alkyl, phenyl or substituted phenyl; and
(ii) an alpha-hydroxy acid and a compound of formula (II)

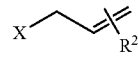

wherein X is halogen and $R^2$ is selected from H, alkyl, phenyl or substituted phenyl.

According to the present invention there is also a method of generating an aerosol comprising nicotine salt particles comprising reacting nicotine with the reaction product of one or both of:

(i) an alpha-keto carboxylic acid and a compound of formula (I)

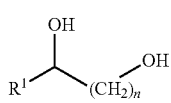

(I)

wherein $R^1$ is selected from alkyl, phenyl or substituted phenyl; and (ii) an alpha-hydroxy acid and a compound of formula (II)

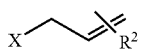

(II)

wherein X is halogen and $R^2$ is selected from H, alkyl, phenyl or substituted phenyl.

According to the present invention there is further provided use of the reaction product of one or both of:

(i) an alpha-keto carboxylic acid and a compound of formula (I)

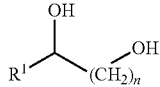

(I)

wherein $R^1$ is selected from alkyl, phenyl or substituted phenyl; and (ii) an alpha-hydroxy acid and a compound of formula (II)

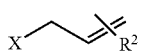

(II)

wherein X is halogen and $R^2$ is selected from H, alkyl, phenyl or substituted phenyl, in an aerosol-generating system for generating an aerosol comprising nicotine salt particles.

According to the present invention there is further provided use of one or both of 2,4-dimethyl-1,3-dioxolane-2-carboxylic acid and 2-(allyloxy)propanoic acid in an aerosol-generating system for generating an aerosol comprising nicotine salt particles.

An alpha-keto carboxylic acid of formula (III) may be reacted with a compound of formula (I), wherein $R^1$ is selected from alkyl, phenyl or substituted phenyl, under acid catalysis to form a reaction product of formula (V):

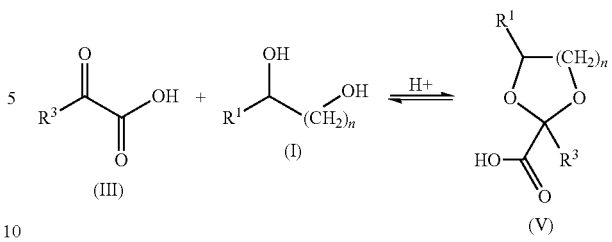

In certain embodiments, the aerosol-generating system according and the aerosol-generating article according to the present invention comprises: a nicotine source; and a delivery enhancing compound source, wherein the delivery enhancing compound source comprises a reaction product of formula (V). In such embodiments, in use, nicotine vapour released from the nicotine source and vapour of the reaction product of formula (V) released from the delivery enhancing compound source react with one another in the gas phase to form an aerosol comprising nicotine salt particles:

nicotine+reaction product of formula(V)→nicotine-[reaction product of formula(V)] salt When the aerosol generated by the in situ reaction between the nicotine vapour released from the nicotine source and the vapour of the reaction product of formula (V) released from the delivery enhancing compound source is inhaled by the user, the nicotine salt particles are hydrolysed to nicotine, the alpha-keto carboxylic acid of formula (III) and the compound of formula (I):

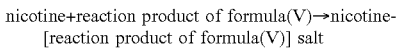
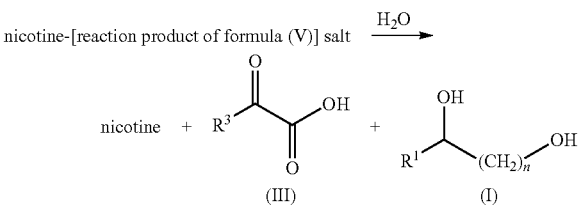

The reaction product of formula (V) is more stable than the alpha-keto carboxylic acid of formula (III). Therefore, inclusion of the reaction product of an alpha-keto carboxylic acid and a compound of formula (I) as a delivery enhancing compound in the aerosol-generating system and the aerosol-generating article according to the present invention advantageously reduces the complexity and cost of manufacturing the aerosol-generating system and the aerosol-generating article according to the present invention compared to devices comprising alpha-keto carboxylic acids, such as pyruvic acid, as a delivery enhancing compound in which the delivery enhancing compound source may need to be housed in a specially adapted container in order to avoid degradation of the alpha-keto carboxylic acid.

The reaction product of formula (V) is also less volatile than the alpha-keto carboxylic acid of formula (III). Therefore, inclusion of the reaction product of an alpha-keto carboxylic acid and a compound of formula (I) as a delivery enhancing compound in the aerosol-generating system and the aerosol-generating article according to the present invention advantageously allows an efficient reaction stoichiometry to be achieved by heating the nicotine source and the delivery enhancing compound source to substantially the same temperature. This advantageously reduces the complexity and cost of manufacturing the aerosol-generating system and the aerosol-generating article according to the present invention compared to devices comprising alpha-keto carboxylic acids, such as pyruvic acid, as a delivery enhancing compound in which the nicotine source and the delivery enhancing compound source may need to be heated to different temperatures in order to achieve an efficient reaction stoichiometry.

In certain preferred embodiments, the delivery enhancing compound comprises the reaction product of: (i) an alpha-keto carboxylic acid and a compound of formula (I), wherein n is an integer from 1 to 4 inclusive and $R^1$ is selected from $C_{1-4}$ alkyl.

In certain preferred embodiments, the delivery enhancing compound comprises the reaction product of: (i) an alpha-keto carboxylic acid of formula (III), wherein $R^3$ is selected from $C_{1-4}$ alkyl, and a compound of formula (I). In one preferred embodiment, the delivery enhancing compound comprises the reaction product of: (i) pyruvic acid and a compound of formula (I).

In certain particularly preferred embodiments, the delivery enhancing compound comprises the reaction product of: (i) an alpha-keto carboxylic acid of formula (III), wherein $R^3$ is selected from $C_{1-4}$ alkyl, and a compound of formula (I), wherein n is an integer from 1 to 4 inclusive and $R^1$ is selected from $C_{1-4}$ alkyl. In one particularly preferred embodiment the delivery enhancing compound comprises the reaction product of: (i) pyruvic acid and propylene glycol.

An alpha-hydroxy acid of formula (IV) may be reacted with a compound of formula (II), wherein X is halogen and $R^2$ is selected from H, alkyl, phenyl or substituted phenyl, to form a reaction product of formula (VI):

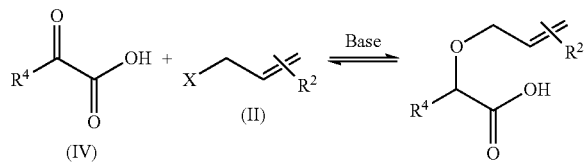

In certain embodiments, the aerosol-generating system according and the aerosol-generating article according to the present invention comprises: a nicotine source; and a delivery enhancing compound source, wherein the delivery enhancing compound source comprises a reaction product of formula (VI). In such embodiments, in use, nicotine vapour released from the nicotine source and vapour of the reaction product of formula (VI) released from the delivery enhancing compound source react with one another in the gas phase to form an aerosol comprising nicotine salt particles:

nicotine+reaction product of formula(VI)→nicotine-[reaction product of formula(VI)] salt When the aerosol generated by the in situ reaction between the nicotine vapour released from the nicotine source and the vapour of the reaction product of formula (VI) released from the delivery enhancing compound source is inhaled by the user, the nicotine salt particles are hydrolysed to nicotine and the alpha-hydroxy acid of formula (IV):

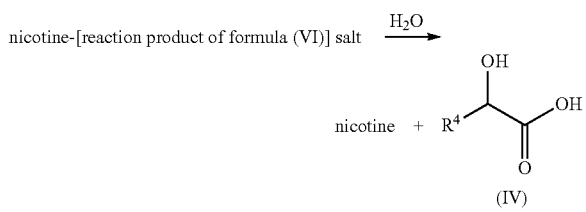

The reaction product of formula (VI) is more stable than the alpha-hydroxy acid of formula (IV). Therefore, inclusion of the reaction product of an alpha-hydroxy acid and a compound of formula (II) as a delivery enhancing compound in the aerosol-generating system and the aerosol-generating article according to the present invention advantageously reduces the complexity and cost of manufacturing the aerosol-generating system and the aerosol-generating article according to the present invention compared to devices comprising alpha-hydroxy acids, such as lactic acid, as a delivery enhancing compound in which the delivery enhancing compound source may need to be housed in a specially adapted container in order to avoid degradation of the alpha-hydroxy acid.

In certain preferred embodiments, the delivery enhancing compound comprises the reaction product of: (ii) an alpha-hydroxy acid and a compound of formula (II), wherein X is Br and $R^2$ is selected from H and $C_{1-4}$ alkyl.

In certain preferred embodiments, the delivery enhancing compound comprises the reaction product of: (ii) an alpha-hydroxy acid of formula (IV), wherein $R^4$ is selected from $C_{1-4}$ alkyl, and a compound of formula (II). In one preferred embodiment, the delivery enhancing compound comprises the reaction product of: (ii) lactic acid and a compound of formula (II).

In certain particularly preferred embodiments, the delivery enhancing compound comprises the reaction product of: (ii) an alpha-hydroxy acid of formula (IV), wherein $R^4$ is selected from $C_{1-4}$ alkyl, and a compound of formula (II), wherein X is Br and $R^2$ is selected from H and $C_{1-4}$ alkyl. In one particularly preferred embodiment the delivery enhancing compound comprises the reaction product of: (ii) lactic acid and allyl bromide.

Preferably, the aerosol-generating system according to the present invention is a pulmonary delivery system for the in situ generation of an aerosol comprising nicotine salt particles that is inhalable into a user's lungs.

As used herein with reference to the present invention, by "in situ" it is meant that, in use, nicotine vapour released from the nicotine source and reaction product vapour released from the delivery enhancing compound source react with one another in the gas phase within the aerosol-generating system according to the present invention to form an aerosol comprising nicotine salt particles.

The aerosol-generating system according to the present invention may be a single-piece system. In such embodiments, the single-piece system comprising the nicotine source and the delivery enhancing compound source and any other components of the aerosol-generating system is discarded after use.

Advantageously, the aerosol-generating system according to the present invention may be a multi-piece system comprising two or more separable pieces that are configured to engage and cooperate with one another to form an aerosol-generating system for the in situ generation of an aerosol comprising nicotine salt particles. Preferably, the multi-piece system comprises two, three or four pieces.

In such embodiments, the multi-piece system may comprise one or more consumable pieces that are discarded after use and one or more reusable pieces. For example, the multi-piece system may comprise a consumable piece comprising the nicotine source and the delivery enhancing compound source and a reusable piece comprising heating means for heating one or both of the nicotine source and the delivery enhancing compound source.

In such embodiments, the multi-piece system may comprise suitable connecting means, such as, for example, mechanical connecting means, to enable the two or more pieces thereof to be detachably connected to one another without adversely impacting the functionality of the system as compared to a single-piece system.

In preferred embodiments, the aerosol-generating system according to the present invention comprises an aerosol-generating article comprising the nicotine source and the delivery enhancing compound source; and an aerosol-generating device configured to receive the aerosol-generating article. In such embodiments, the aerosol-generating article and the aerosol-generating device are configured to engage and cooperate with one another to form an aerosol-generating system for the in situ generation of an aerosol comprising nicotine salt particles.

In particularly preferred embodiments, the aerosol-generating system according to the present invention comprises a consumable aerosol-generating article comprising the nicotine source and the delivery enhancing compound source; and a reusable aerosol-generating device configured to receive the aerosol-generating article.

As used herein with reference to the present invention, the term "aerosol-generating device" refers to a device that is configured to interact with an aerosol-generating article comprising a nicotine source and a delivery enhancing compound source to generate an aerosol comprising nicotine salt particles.

As used herein with reference to the present invention, the term "aerosol-generating article" refers to an article comprising a nicotine source capable of releasing nicotine and a delivery enhancing compound source capable of releasing the reaction product, wherein the nicotine and reaction product can react with one another in the gas phase to form an aerosol comprising nicotine salt particles.

Generally, the aerosol-generating system according to the present invention may comprise a combination of: any aerosol-generating article comprising a nicotine source and a delivery enhancing compound source, wherein the delivery enhancing compound source comprises the reaction product of:

(i) an alpha-keto carboxylic acid and a compound of formula (I)

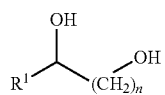

(I)

wherein $R^1$ is selected from alkyl, phenyl or substituted phenyl; or (ii) an alpha-hydroxy acid and a compound of formula (II)

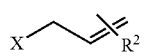

(II)

wherein X is halogen and $R^2$ is selected from H, alkyl, phenyl or substituted phenyl; and any aerosol-generating device configured to receive the aerosol-generating article.

As used herein with reference to embodiments of the present invention, the terms "upstream", "downstream", "proximal" and "distal" are used to describe the relative positions of components, or portions of components, of the aerosol-generating system, the aerosol-generating article and the aerosol-generating device according to the present invention.

The aerosol-generating system according to the present invention comprises a proximal end through which, in use, an aerosol exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the aerosol-generating system and exits the aerosol-generating system at the proximal end. Components, or portions of components, of the aerosol-generating system may be described as being upstream or downstream of one another based on their relative positions between the proximal end and the distal end of the aerosol-generating system.

As used herein with reference to the present invention, the term "longitudinal" is used to describe the direction between the proximal end and the opposed distal end of the aerosol-generating system. As used herein with reference to the present invention, the term "transverse" is used to describe the direction perpendicular to the longitudinal direction.

As used herein with reference to the present invention, by "length" is meant the maximum longitudinal dimension between the distal end and the proximal end of components, or portions of components, of the aerosol-generating system.

Preferably, the aerosol-generating system according to the present invention further comprises heating means for heating one or both of the nicotine source and the delivery enhancing compound source. Heating one or both of the nicotine source and the delivery enhancing compound source to a temperature above ambient temperature allows control of the amount of nicotine vapour and reaction product vapour released from the nicotine source and the delivery enhancing compound source, respectively. This advantageously enables the vapour concentrations of the nicotine and the reaction product to be controlled and balanced proportionally to yield an efficient reaction stoichiometry. This advantageously improves the efficiency of the formation of an aerosol and the consistency of nicotine delivery to a user. It also advantageously reduces the delivery of unreacted nicotine vapour and unreacted reaction product vapour to a user.

In preferred embodiments, the heating means is configured to heat both the nicotine source and the delivery enhancing compound source. In certain preferred embodiments, the heating means is configured to heat both the nicotine source and the delivery enhancing compound source to a temperature of below about 250 degrees Celsius (° C.). In certain particularly preferred embodiments, the heating means is configured to heat both the nicotine source and the delivery enhancing compound source to a temperature of between about 80° C. and about 150° C.

Advantageously, the heating means is configured to heat the nicotine source and the delivery enhancing compound source to substantially the same temperature.

As used herein with reference to the present invention, by "substantially the same temperature" it is meant that the difference in temperature of the nicotine source and the delivery enhancing compound source measured at corresponding locations relative to the heating means is less than about 3° C. In certain preferred embodiments, the heating means is configured to heat the nicotine source and the delivery enhancing compound source to the same temperature.

The heating means may have any shape suitable to heat one or both of the nicotine source and the delivery enhancing compound source.

Preferably, the heating means comprises a single heater. As described further below, this advantageously provides for simple construction of the aerosol-generating system and the aerosol-generating article according to the present invention.

The heating means may comprise an external heater. As used herein with reference to the present invention, the term "external heater" refers to a heater that in use is positioned externally to the nicotine source and the delivery enhancing compound source of the aerosol-generating system.

Alternatively or in addition, the heating means may comprise an internal heater. As used herein with reference to the present invention, the term "internal heater" refers to a heater that in use is positioned internally to one or both of the nicotine source and the delivery enhancing compound source of the aerosol-generating system.

In certain preferred embodiments, the aerosol-generating system according to the present invention comprises an aerosol-generating article comprising the nicotine source and the delivery enhancing compound source and an aerosol-generating device configured to receive the aerosol-generating article, wherein the aerosol-generating device comprises heating means for heating one or both of the nicotine source and the delivery enhancing compound source of the aerosol-generating article. In such embodiments, the aerosol-generating device may comprise heating means comprising an external heater that in use is positioned externally to the aerosol-generating article. Alternatively or in addition, the aerosol-generating device may comprise heating means comprising an internal heater that in use is positioned internally to the aerosol-generating article.

Preferably, the aerosol-generating device comprises heating means comprising a single heater. More preferably, the aerosol-generating device comprises heating means comprising a single internal heater. In such embodiments, the aerosol-generating device may advantageously comprise guide means to facilitate proper alignment of the single internal heater with the aerosol-generating article.

The aerosol-generating system according to the present invention may further comprise a power supply for supplying power to the heating means and a controller configured to control a supply of power from the power supply to the heating means. Alternatively, the aerosol-generating system according to the present invention may comprise a controller configured to control a supply of power from an external power supply to the heating means.

The aerosol-generating system according to the present invention may further comprise one or more temperature sensors configured to sense the temperature of at least one of the heating means, the nicotine source and the delivery enhancing compound source. In such embodiments, the controller may be configured to control a supply of power to the heating means based on the sensed temperature.

Where the aerosol-generating system according to the present invention comprises an aerosol-generating article comprising the nicotine source and the delivery enhancing compound source and an aerosol-generating device comprising the heating means, the aerosol-generating device preferably comprises the power supply, the controller and the one or more temperature sensors, where present.

Preferably, the heating means comprises an electric heating element powered by an electric power supply. Where the heating means comprises an electric heating element, the aerosol-generating system according to the present invention may further comprise an electric power supply and a controller comprising electronic circuitry configured to control the supply of electric power from the electric power supply to the electric heating element. Any suitable electronic circuitry may be used in order to control the supply of power to the electric heating element. The electronic circuitry may be programmable.

The power supply may be a DC voltage source. In preferred embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging. Where the aerosol-generating system according to the present invention comprises an aerosol-generating article comprising the nicotine source and the delivery enhancing compound source, and an aerosol-generating device comprising heating means for heating one or both of the nicotine source and the delivery enhancing compound source of the aerosol-generating article, the power supply may have a capacity that allows for the storage of enough energy for use of the aerosol-generating device with one or more aerosol-generating articles.

Preferably, the electric heating element comprises an electrically resistive material. The electric heating element may comprise a non-elastic material, for example a ceramic sintered material, such as alumina ($Al_2O_3$) and silicon nitride ($Si_3N_4$), or printed circuit board or silicon rubber. Alternatively, the electric heating element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

In certain preferred embodiments, the heating means comprises a single heater, wherein the single heater is an elongate internal electric heating element. In certain particularly preferred embodiments, the heating means comprises a single heater, wherein the single heater is an elongate internal electric heating element having a width that is greater than the thickness thereof so that the elongate internal electric heating element is in the form of a heater blade.

Alternatively, the heating means may be powered by a non-electric power supply, such as a combustible fuel. For example, the heating means may comprise a thermally conductive element that is heated by combustion of a gaseous fuel.

Alternatively, the heating means may be a non-electric heating means, such as a chemical heating means.

In certain embodiments the heating means may comprise a heat sink or heat exchanger configured to transfer thermal energy from an external heat source to one or both of the nicotine source and the delivery enhancing compound source. The heat sink or heat exchanger may be formed of any suitable thermally conductive material. Suitable thermally conductive materials include, but are not limited to, metals, such as aluminium and copper.

Where the aerosol-generating system according to the present invention comprises an aerosol-generating article comprising the nicotine source and the delivery enhancing compound source, and an aerosol-generating device comprising heating means for heating one or both of the nicotine source and the delivery enhancing compound source of the aerosol-generating article, the heating means preferably does not project from the aerosol-generating device.

The nicotine source may comprise one or more of nicotine, nicotine base, a nicotine salt, such as nicotine-HCl, nicotine-tartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract. Advantageously, the nicotine source comprises pure nicotine.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The nicotine source may comprise a sorption element and nicotine sorbed on the sorption element.

As used herein with reference to the present invention, by "sorbed" it is meant that a compound is adsorbed on the surface of the sorption element, or absorbed in the sorption element, or both adsorbed on and absorbed in the sorption element.

The sorption element may be formed from any suitable material or combination of materials. For example, the sorption element may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The sorption element may be a porous sorption element. For example, the sorption element may be a porous sorption element comprising one or more materials selected from the group consisting of porous plastic materials, porous polymer fibres and porous glass fibres.

The sorption element is preferably chemically inert with respect to nicotine.

The sorption element may have any suitable size and shape.

In certain embodiments the sorption element may be a substantially cylindrical plug. For example, the sorption element may be a porous substantially cylindrical plug.

As used herein with reference to the present invention, the terms "cylinder" and "cylindrical" refer to a substantially right circular cylinder with a pair of opposed substantially planar end faces.

In other embodiments the sorption element may be a substantially cylindrical hollow tube. For example, the sorption element may be a porous substantially cylindrical hollow tube.

The size, shape and composition of the sorption element may be chosen to allow a desired amount of nicotine to be sorbed on the sorption element.

The sorption element advantageously acts as a reservoir for the nicotine.

The delivery enhancing compound source may comprise a sorption element and the reaction product sorbed on the sorption element.

Preferably, the delivery enhancing compound is adsorbed on the sorption element.

The sorption element may be formed from any suitable material or combination of materials, for example those listed above.

The sorption element is preferably chemically inert with respect to the reaction product.

The sorption element may have any suitable size and shape.

In certain embodiments the sorption element may be a substantially cylindrical plug. For example, the sorption element may be a porous substantially cylindrical plug.

In other embodiments the sorption element may be a substantially cylindrical hollow tube. For example, the sorption element may be a porous substantially cylindrical hollow tube.

The size, shape and composition of the sorption element may be chosen to allow a desired amount the reaction product to be sorbed on the sorption element.

The sorption element advantageously acts as a reservoir for the reaction product.

The aerosol-generating system according to the present invention may comprise a first compartment comprising the nicotine source and a second compartment comprising the delivery enhancing compound source.

As used herein with reference to the present invention, the term "compartment" is used to describe a chamber or container within the aerosol-generating system comprising the nicotine source or the delivery enhancing compound source.

The first compartment and the second compartment of the aerosol-generating system may abut one another. Alternatively, the first compartment and the second compartment of the aerosol-generating system may be spaced apart from one another.

One or both of the first compartment and the second compartment of the aerosol-generating system may be sealed by one or more frangible barriers. The one or more frangible barriers may be formed from any suitable material. For example, the one or more frangible barriers may be formed from a metal foil or film.

In such embodiments, the aerosol-generating system according to the present invention may further comprise one or more piercing members configured to rupture the one or more frangible barriers.

Alternatively or in addition, one or both of the first compartment and the second compartment of the aerosol-generating system may be sealed by one or more removable barriers. For example, one or both of the first compartment and the second compartment of the aerosol-generating system may be sealed by one or more peel-off seals. The one or more removable barriers may be formed from any suitable material. For example, the one or more removable barriers may be formed from a metal foil or film.

As described further below, the first compartment and the second compartment may be arranged in series or parallel within the aerosol-generating system.

As used herein with reference to the present invention, by "series" it is meant that the first compartment and the second compartment are arranged within the aerosol-generating system according to the present invention so that in use an air stream drawn through the aerosol-generating system passes through one of the first compartment and the second compartment and then passes through the other of the first compartment and the second compartment. Nicotine vapour is released from the nicotine source in the first compartment into the air stream drawn through the aerosol-generating system and reaction product vapour is released from the delivery enhancing compound source in the second compartment into the air stream drawn through the aerosol-generating system. The nicotine vapour reacts with the reaction product vapour in the gas phase to form an aerosol, which is delivered to a user.

Where the first compartment and the second compartment are arranged in series within the aerosol-generating system, the second compartment may be located downstream of the first compartment so that in use an air stream drawn through the aerosol-generating article passes through the first compartment and then passes through the second compartment. In such embodiments, the nicotine vapour may react with the reaction product vapour in the second compartment to form an aerosol. In such embodiments the aerosol-generating system may further comprise a third compartment downstream of the second compartment and the nicotine vapour may alternatively or in addition react with the reaction product vapour in the third compartment to form an aerosol.

Alternatively, where the first compartment and the second compartment are arranged in series within the aerosol-generating system, the second compartment may be located upstream of the first compartment so that in use an air stream drawn through the aerosol-generating article passes through the second compartment and then passes through the first compartment. In such embodiments, the reaction product vapour may react with the nicotine vapour in the second compartment to form an aerosol. In such embodiments the aerosol-generating system may further comprise a third compartment downstream of the first compartment and the reaction product vapour may alternatively or in addition react with the nicotine vapour in the third compartment to form an aerosol.

As used herein with reference to the present invention, by "parallel" it is meant that the first compartment and the second compartment are arranged within the aerosol-generating system according to the present invention so that in use a first air stream drawn through the aerosol-generating system passes through the first compartment and a second air stream drawn through the aerosol-generating system passes through the second compartment. Nicotine vapour is released from the nicotine source in the first compartment into the first air stream drawn through the aerosol-generating system and reaction product vapour is released from the delivery enhancing compound source in the second compartment into the second air stream drawn through the aerosol-generating system. The nicotine vapour in the first air stream reacts with the reaction product vapour in the second air stream in the gas phase to form an aerosol, which is delivered to a user.

In such embodiments the aerosol-generating system may further comprise a third compartment downstream of the first compartment and the second compartment and the nicotine vapour in the first air stream may mix and react with the reaction product vapour in the second air stream in the third compartment to form an aerosol.

In certain preferred embodiments, the aerosol-generating system according to the present invention comprises: a housing comprising: an air inlet; a first compartment in communication with the air inlet, the first compartment comprising the nicotine source; a second compartment in communication with the first compartment, the second compartment comprising the delivery enhancing compound source; and an air outlet, wherein the air inlet and the air outlet are in communication with each other and configured so that air may pass into the housing through the air inlet, through the housing and out of the housing through the air outlet.

As used herein with reference to the present invention, the term "air inlet" is used to describe one or more apertures through which air may be drawn into the aerosol-generating system.

As used herein with reference to the present invention, the term "air outlet" is used to describe one or more apertures through which air may be drawn out of the aerosol-generating system.

In such embodiments, the first compartment and the second compartment are arranged in series from air inlet to air outlet within the housing. That is, the first compartment is downstream of the air inlet, the second compartment is downstream of the first compartment and the air outlet is downstream of the second compartment. In use, a stream of air is drawn into the housing through the air inlet, downstream through the first compartment and the second compartment and out of the housing through the air outlet.

In such embodiments, the aerosol-generating system may further comprise a third compartment in communication with: the second compartment; and the air outlet. In use in such embodiments, a stream of air is drawn into the housing through the air inlet, downstream through the first compartment, the second compartment and the third compartment and out of the housing through the air outlet.

In such embodiments, the aerosol-generating system may further comprise a mouthpiece in communication with: the second compartment or the third compartment, where present, and the air outlet. In use in such embodiments, a stream of air is drawn into the housing through the air inlet, downstream through the first compartment, the second compartment, the third compartment, where present, and the mouthpiece and out of the housing through the air outlet.

In other preferred embodiments, the aerosol-generating system according to the present invention comprises: a housing comprising: an air inlet; a second compartment in communication with the air inlet, the second compartment comprising the delivery enhancing compound source; a first compartment in communication with the second compartment, the first compartment comprising the nicotine source; and an air outlet, wherein the air inlet and the air outlet are in communication with each other and configured so that air may pass into the housing through the air inlet, through the housing and out of the housing through the air outlet.

In such embodiments, the second compartment and the first compartment are arranged in series from air inlet to air outlet within the housing. That is, the second compartment is downstream of the air inlet, the first compartment is downstream of the second compartment and the air outlet is downstream of the first compartment. In use, a stream of air is drawn into the housing through the air inlet, downstream through the second compartment and the first compartment and out of the housing through the air outlet.

In such embodiments, the aerosol-generating system may further comprise a third compartment in communication with: the first compartment; and the air outlet. In use in such embodiments, a stream of air is drawn into the housing through the air inlet, downstream through the second compartment, the first compartment and the third compartment and out of the housing through the air outlet.

The aerosol-generating system may further comprise a mouthpiece in communication with: the first compartment or the third compartment, where present; and the air outlet. In use in such embodiments, a stream of air is drawn into the housing through the air inlet, downstream through the second compartment, the first compartment, the third compartment, where present, and the mouthpiece and out of the housing through the air outlet.

In further preferred embodiments, the aerosol-generating system according to the present invention comprises: a housing comprising: an air inlet; a first compartment in communication with the air inlet, the first compartment comprising the nicotine source; a second compartment in communication with the air inlet, the second compartment comprising the delivery enhancing compound source; and an air outlet, wherein the air inlet and the air outlet are in communication with each other and configured so that air may pass into the housing through the air inlet, through the housing and out of the housing through the air outlet.

In such embodiments, the first compartment and the second compartment are arranged in parallel from air inlet to air outlet within the housing. The first compartment and the second compartment are both downstream of the air inlet and upstream of the air outlet. In use, a stream of air is drawn into the housing through the air inlet, a first portion of the stream of air is drawn downstream through the first compartment and a second portion of the stream of air is drawn downstream through the second compartment.

In such embodiments, the aerosol-generating system may further comprise a third compartment in communication with: one or both of the first compartment and the second compartment; and the air outlet.

In such embodiments, the aerosol-generating system may further comprise a mouthpiece in communication with: the first compartment and the second compartment, or the third compartment, where present; and the air outlet.

In yet further preferred embodiments, the aerosol-generating system according to the present invention comprises: a housing comprising: a first air inlet; a second air inlet; a first compartment in communication with the first air inlet, the first compartment comprising the nicotine source; a second compartment in communication with the second air inlet, the second compartment comprising the delivery enhancing compound source; and an air outlet, wherein the first air inlet, the second air inlet and the air outlet are in communication with each other and configured so that air may pass into the housing through the first air inlet, through the housing and out of the housing through the air outlet and air may pass into the housing through the first air inlet, through the housing and out of the housing through the air outlet.

In such embodiments, the first compartment and the second compartment are arranged in parallel within the housing. The first compartment is downstream of the first air inlet and upstream of the air outlet and the second compartment is downstream of the second air inlet and upstream of the air outlet. In use, a first stream of air is drawn into the housing through the first air inlet and downstream through the first compartment and a second stream of air is drawn into the housing through the second air inlet and downstream through the second compartment.

In such embodiments, the aerosol-generating system may further comprise a third compartment in communication with: one or both of the first compartment and the second compartment; and the air outlet.

In such embodiments, the aerosol-generating system may further comprise a mouthpiece in communication with: the first compartment and the second compartment, or the third compartment, where present; and the air outlet.

Where the aerosol-generating system according to the present invention comprises a housing, the housing may be designed to be grasped or held by a user.

Preferably, the housing is substantially cylindrical.

Where the aerosol-generating system according to the present invention comprises a third compartment, the third compartment may comprise one or more aerosol-modifying agents. Suitable aerosol-modifying agents include, but are not limited to: flavourants; sorbents and chemesthetic agents.

As used herein with reference to the present invention, the term "flavourant" is used to describe any agent that, in use, imparts one or both of a taste or aroma to an aerosol generated by the reaction between nicotine vapour released from the nicotine source and reaction product vapour released from the delivery enhancing compound source of the aerosol-generating system according to the present invention.

As used herein with reference to the present invention, the term "chemesthetic agent" is used to describe any agent that, in use, is perceived in the oral or olfactory cavities of a user by means other than, or in addition to, perception via taste receptor or olfactory receptor cells. Perception of chemesthetic agents is typically via a "trigeminal response," either via the trigeminal nerve, glossopharyngeal nerve, the vagus nerve, or some combination of these. Typically, chemesthetic agents are perceived as hot, spicy, cooling, or soothing sensations.

For example, the third compartment may comprise one or more sorbents, such as activated carbon, one or more flavourants that provide a cooling chemesthetic effect, such as menthol, or a combination thereof.

Where the aerosol-generating system according to the present invention comprises a mouthpiece, the mouthpiece may comprise a filter. The filter may have a low particulate filtration efficiency or very low particulate filtration efficiency. Alternatively, the mouthpiece may comprise a hollow tube.

In preferred embodiments, the aerosol-generating system according to the present invention comprises an aerosol-generating article comprising the nicotine source and the delivery enhancing compound source; and an aerosol-generating device configured to receive the aerosol-generating article In such embodiments, the aerosol-generating article is preferably substantially cylindrical. The aerosol-generating article may simulate the shape and dimensions of a tobacco smoking article, such as a cigarette, a cigar, a cigarillo or a pipe, or a cigarette pack. In certain preferred embodiments, the aerosol-generating article simulates the shape and dimensions of a cigarette.

In such embodiments, the aerosol-generating device preferably comprises a cavity configured to receive the aerosol-generating article. In particular, the aerosol-generating device preferably comprises a cavity configured to receive the nicotine source and the delivery enhancing compound source of the aerosol-generating article.

Preferably, the cavity of the aerosol-generating device is substantially cylindrical.

Preferably, the cavity of the aerosol-generating device has a diameter substantially equal to or slightly greater than the diameter of the aerosol-generating article.

Preferably, the length of the cavity of the aerosol-generating device is less than the length of the aerosol-generating article so that when the aerosol-generating article is received in the cavity of the aerosol-generating device the proximal or downstream end of the aerosol-generating article projects from the cavity of the aerosol-generating device.

Where the aerosol-generating device comprises heating means for heating one or both of the nicotine source and the delivery enhancing compound source of the aerosol-generating article, the heating means may comprise an external heater positioned about a perimeter of the cavity. Alternatively, the heating means may comprise an internal heater positioned within the cavity.

The aerosol-generating article may comprise a first compartment comprising the nicotine source and a second compartment comprising the delivery enhancing compound source as described above. As previously described, the first compartment and the second compartment may be arranged in series or parallel within the aerosol-generating article.

The aerosol-generating article may further comprise a third compartment comprising an aerosol-modifying agent as previously described.

As previously described, one or both of the first compartment comprising the nicotine source and the second compartment comprising the delivery enhancing compound source may be sealed by one or more frangible barriers, one or more removable barriers or a combination thereof.

Where one or both of the first compartment and the second compartment are sealed by one or more frangible barriers, the aerosol-generating device preferably further comprises one or more piercing members configured to rupture the one or more frangible barriers sealing one or both of the first compartment and the second compartment.

Where the first compartment and the second compartment are arranged in series within the aerosol-generating article, the aerosol-generating device may comprise a piercing member positioned centrally within the cavity of the aerosol-generating device, along the major axis of the cavity, for piercing the first compartment and the second compartment of the aerosol-generating article.

Where the first compartment and the second compartment of the aerosol-generating article are arranged in parallel within the aerosol-generating article, the aerosol-generating device may comprise a piercing member comprising a first piercing member positioned within the cavity of the aerosol-generating device for piercing the first compartment of the aerosol-generating article and a second piercing member positioned within the cavity of the aerosol-generating device for piercing the second compartment of the aerosol-generating article.

In certain embodiments the aerosol-generating article comprises or consists of a cartridge comprising the nicotine source and the delivery enhancing compound source.

In such embodiments, the first compartment and the second compartment are preferably arranged in parallel within the cartridge.

The cartridge may further comprise a third compartment comprising an aerosol-modifying agent. In such embodiments the first compartment, the second compartment and the third compartment are preferably arranged in parallel within the cartridge.

In certain preferred embodiments the cartridge is substantially cylindrical and the first compartment, the second compartment and, where present, the third compartment extend longitudinally between the opposed substantially planar end faces of the cartridge.

In certain embodiments the cartridge further comprises a cavity and the aerosol-generating device comprises a single heater configured to be received in the cavity.

In certain preferred embodiments, the aerosol-generating system comprises: an aerosol-generating article comprising a cartridge comprising: a first compartment comprising a nicotine source; a second compartment comprising a delivery enhancing compound source, wherein the delivery enhancing compound source comprises the reaction product of:

(i) an alpha-keto carboxylic acid and a compound of formula (I)

wherein $R^1$ is selected from alkyl, phenyl or substituted phenyl; or (ii) an alpha-hydroxy acid and a compound of formula (II)

wherein X is halogen and $R^2$ is selected from H, alkyl, phenyl or substituted phenyl; and a cavity; and an aerosol-generating device comprising: a body portion comprising a single heater; and a mouthpiece portion configured for engagement with the body portion, wherein the aerosol-generating device is configured to receive the aerosol-generating article such that the single heater of the body portion of the aerosol-generating device is received in the cavity of the cartridge of the aerosol-generating article.

In such embodiments, the aerosol-generating article may be received entirely within the body portion of the aerosol-generating device or entirely within the mouthpiece portion of the aerosol-generating device or partially within the body portion of the aerosol-generating device and partially within the mouthpiece portion of the aerosol-generating device.

In such embodiments, the aerosol-generating device may further comprise a guide portion configured for engagement with the body portion to facilitate proper alignment of the single heater with the cavity in the cartridge of the aerosol-generating article.

In certain preferred embodiments, the single heater is an internal electric heating element configured to be received in the cavity of the cartridge of the aerosol-generating article. In certain particularly preferred embodiments, the single heater is an elongate internal electric heating element in the form of a heater blade configured to be received in the cavity of the cartridge of the aerosol-generating article. In such embodiments, the cavity in the cartridge of the aerosol-generated article may be configured as an elongate slot.

In preferred embodiments in which the cartridge is substantially cylindrical, the cavity in the cartridge preferably extends along the longitudinal axis of the cartridge. In such embodiments the first compartment, the second compartment and, where present, the third compartment are preferably disposed around the cavity in the cartridge.

For the avoidance of doubt, features described above in relation to one aspect of the invention may also be applicable to other aspects of the invention. In particular, features described above in relation to the aerosol-generating system according to the present invention may also relate, where appropriate, to one or both of the aerosol-generating article and the aerosol-generating device of the aerosol-generating system according of the present invention, and vice versa.

EXAMPLE 1

2,4-dimethyl-1,3-dioxolane-2-carboxylic acid is prepared from pyruvic acid and propylene glycol under acid catalysis The 2,4-dimethyl-1,3-dioxolane-2-carboxylic acid is reacted with nicotine in the gas phase to form an aerosol of nicotine 2,4-dimethyl-1,3-dioxolane-2-carboxylate salt particles for inhalation by a user. Upon inhalation of the aerosol by a user, the nicotine 2,4-dimethyl-1,3-dioxolane-2-carboxylate salt particles are hydrolysed to nicotine, pyruvic acid and propylene glycol.

EXAMPLE 2

2-(allyloxy)propanoic acid is prepared from lactic acid and allyl bromide

The 2-(allyloxy)propanoic acid is reacted with nicotine in the gas phase to form an aerosol of nicotine 2-(allyloxy) propanoate salt particles. Upon inhalation of the aerosol by a user, the nicotine 2-(allyloxy)propanoate salt particles are hydrolysed to nicotine and lactic acid.

The boiling points of 2,4-dimethyl-1,3-dioxolane-2-carboxylic acid and 2-(allyloxy)propanoic acid are similar to the boiling point of nicotine. Therefore, inclusion of one or both of 2,4-dimethyl-1,3-dioxolane-2-carboxylic acid and 2-(allyloxy)propanoic acid as a delivery enhancing compound in the aerosol-generating system and the aerosol-generating article according to the present invention advantageously allows an efficient reaction stoichiometry to be achieved by heating the nicotine source and the delivery enhancing compound source to substantially the same temperature. This advantageously reduces the complexity and cost of manufacturing the aerosol-generating system and the aerosol-generating article according to the present invention compared to devices in which the nicotine source and the delivery enhancing compound source may need to be heated to different temperatures in order to achieve an efficient reaction stoichiometry.

Figure 2:
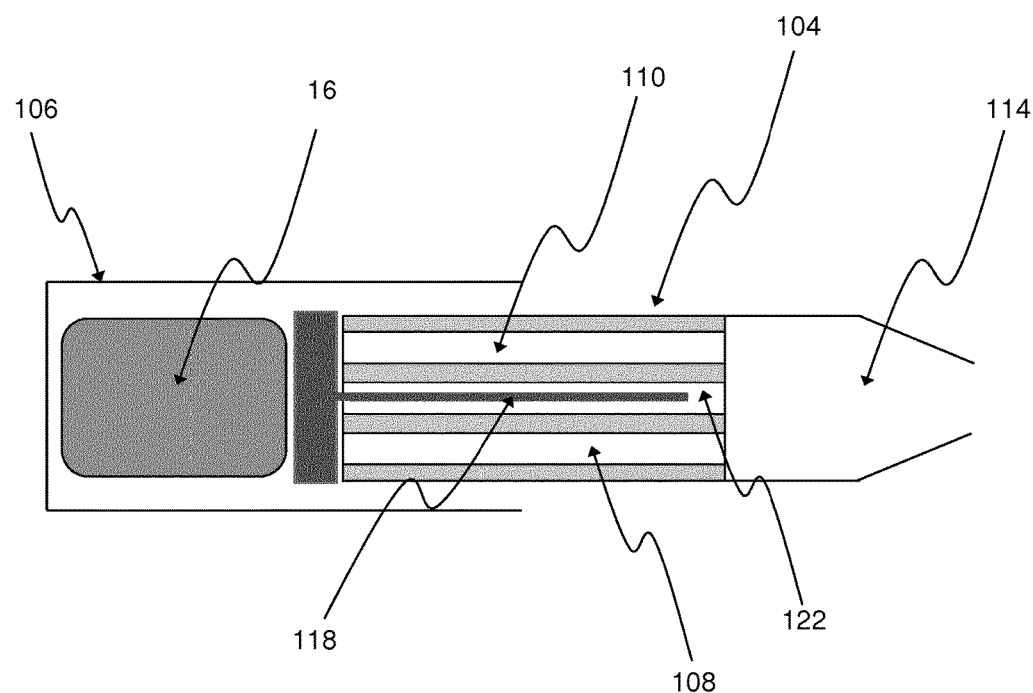

The invention will now be further described with reference to the accompanying drawings in which:

FIG. 1 shows a schematic longitudinal cross-section of an aerosol-generating system according to a first embodiment of the invention comprising: an aerosol-generating article comprising a nicotine source and a delivery enhancing compound source; and an aerosol-generating device configured to receive the aerosol-generating article; and FIG. 2 shows a schematic longitudinal cross-section of an aerosol-generating system according to a second embodiment of the invention comprising: an aerosol-generating article comprising a nicotine source and a delivery enhancing compound source; and an aerosol-generating device configured to receive the aerosol-generating article.

The aerosol-generating system according to the first embodiment of the present invention shown in FIG. 1 generally comprises an aerosol-generating article 4 and an aerosol-generating device 6, which are configured to engage and cooperate with one another to form the aerosol-generating system.

The aerosol-generating article 4 is configured as a one-piece consumable that is discarded after use. The aerosol-generating article 4 has an elongate cylindrical shape and comprises a housing comprising: a first compartment 8 comprising a nicotine source; a second compartment 10 comprising a delivery enhancing compound source, wherein the delivery enhancing compound source comprises 2,4- dimethyl-1,3-dioxolane-2-carboxylic acid; a third compartment 12; and a mouthpiece 14.

The first compartment 8, the second compartment 10, the third compartment 12 and the mouthpiece 14 are arranged in series and in coaxial alignment within the aerosol-generating article 4. The first compartment 8 is located at the distal end of the aerosol-generating article 4. The second compartment 10 is located immediately downstream of the first compartment 8. The third compartment 12 is located immediately downstream of the second compartment 10. The mouthpiece 14 is located immediately downstream of the third compartment 12 at the proximal end of the aerosol-generating article 4.

The nicotine source comprises a sorption element, such as a PTFE wick, with nicotine adsorbed thereon, which is inserted into the first compartment 8. The delivery enhancing compound source comprises a sorption element, such as a PTFE wick, with 2,4-dimethyl-1,3-dioxolane-2-carboxylic acid adsorbed thereon, which is inserted into the second compartment 10.

The aerosol-generating device 6 comprises a housing comprising an elongate cylindrical cavity in which the aerosol-generating article 4 is received. As shown in FIG. 2, the length of the cavity is less than the length of the aerosol-generating article 4 so that when the aerosol-generating article 4 is inserted into the aerosol-generating device 6 the proximal end of the aerosol-generating article 4 protrudes from the cavity.

The aerosol-generating device 6 further comprises a power supply 16, a controller (not shown), a single heater 18 configured to heat both the nicotine source and the delivery enhancing compound source of the aerosol-generating article 4, and a piercing element 20. The power supply 16 is a battery and the controller comprises electronic circuitry and is connected to the power supply 16 and the single heater 18.

The single heater is an electric heating element positioned about the perimeter of a portion of the cavity, which extends fully around the circumference of the cavity. As shown in FIG. 1, the electric heating element is positioned so that it circumscribes the first compartment 8 and the second compartment 10 of the aerosol-generating article 4.

The piercing element 20 is positioned centrally within the cavity of the aerosol-generating device 6 and extends along the major axis of the cavity.

In use, as the aerosol-generating article 4 is inserted into the cavity of the aerosol-generating device 6 the piercing member 20 of the aerosol-generating device 6 is inserted into the aerosol-generating article 4 and pierces the first compartment 8 comprising the nicotine and the second compartment 10 comprising the delivery enhancing compound source. This allows a user to draw air into the housing of the aerosol-generating article 4 through the distal or upstream end thereof, downstream through the first compartment 8, the second compartment 10 and the third compartment 12 and out of the housing through the mouthpiece 14 at the proximal end thereof.

Once the aerosol-generating article 4 is inserted into the cavity of the aerosol-generating device 6, the electric heating element of the aerosol-generating device 6 heats the nicotine source in the first compartment 8 and the delivery enhancing compound source in the second compartment 10 of the aerosol-generating article 4 to substantially the same temperature.

In use, the user draws on the mouthpiece 14 at the proximal and of the aerosol-generating article 4 to draw air through the first compartment 8 comprising the nicotine source and the second compartment 10 comprising the delivery enhancing compound source. As the user draws air through the aerosol-generating article 4, nicotine vapour is released from the nicotine source in the first compartment 8 into the air stream drawn through the aerosol-generating article 4 and 2,4-dimethyl-1,3-dioxolane-2-carboxylic acid vapour is released from the delivery enhancing compound source in the second compartment 10 into the air stream drawn through the aerosol-generating article 4. The nicotine vapour reacts with the 2,4-dimethyl-1,3-dioxolane-2-carboxylic acid vapour in the gas phase in the second compartment 10 and the third compartment 12 to form an aerosol of nicotine 2,4-dimethyl-1,3-dioxolane-2-carboxylate salt particles, which is delivered to the user through the mouthpiece 14 at the proximal end of the aerosol-generating article 4.

The aerosol-generating system according to the second embodiment of the present invention shown in FIG. 2 generally comprises an aerosol-generating article 104 and an aerosol-generating device 106, which are configured to engage and cooperate with one another to form the aerosol-generating system.

The aerosol-generating article 104 is configured as a one-piece consumable that is discarded after use. The aerosol-generating article 104 comprises a cartridge comprising a first compartment 108 comprising a nicotine source, a second compartment 110 comprising a delivery enhancing compound source, wherein the delivery enhancing compound source comprises 2-(allyloxy)propanoic acid, and a mouthpiece 114.

The first compartment 108 comprising the nicotine source and the second compartment 110 comprising the delivery enhancing compound source are arranged in parallel within the cartridge at the distal end of the aerosol-generating article 104. The mouthpiece 114 is located downstream of the first compartment 108 comprising the nicotine source and the second compartment 110 comprising the delivery enhancing compound source at the proximal end of the aerosol-generating article 104.

The cartridge of the aerosol-generating article 104 comprises a cavity 122, for example configured as a slot. As shown in FIG. 2, the cavity 122 extends along the major axis of the cartridge between the first compartment 108 comprising the nicotine source and the second compartment 110 comprising the delivery enhancing compound source.

The nicotine source comprises a sorption element, such as a PTFE wick, with nicotine adsorbed thereon, which is inserted into the first compartment 108. The delivery enhancing compound source comprises a sorption element, such as a PTFE wick, with 2-(allyloxy)propanoic acid adsorbed thereon, which is inserted into the second compartment 110.

The aerosol-generating device 106 comprises a housing comprising a cylindrical cavity in which the cartridge of the aerosol-generating article 104 is received. As shown in FIG. 2, the length of the cavity is less than the length of the aerosol-generating article 104 so that when the cartridge of the aerosol-generating article 104 is inserted into the aerosol-generating device 4 at least the mouthpiece 114 at the proximal end of the aerosol-generating article 104 projects from the cavity.

The aerosol-generating device 106 comprises a single heater 118 configured to heat both the nicotine source and the delivery enhancing compound source of the aerosol-generating article 104. As shown in FIG. 2, the single heater is positioned centrally within the cavity of the aerosol-generating device 104 and extends along the major axis of the cavity. The single heater is an elongate electric heating element in the form of a heater blade. In the second embodiment of the invention shown in FIG. 2, the single heater 118 projects from the housing of the aerosol-generating device 106. However, in alternative embodiments (not shown), the length of the single heater 118 may be less than the length of the cavity so that the single heater does not project from the housing of the aerosol-generating device 106. The aerosol-generating device 106 further comprises a power supply 116 in the form of a battery and a controller (not shown) comprising electronic circuitry, which is connected to the power supply 116 and the single heater.

The opposed substantially planar end faces of the cartridge may be sealed by removable barriers, such as peel-off seals (not shown), which may be removed before the cartridge of the aerosol-generating article 104 is inserted into the cavity of the aerosol-generating device 106 to allow a user to draw air though the first compartment 108 comprising the nicotine source and the second compartment 110 comprising the delivery enhancing source and out of the aerosol-generating article 104 through the mouthpiece 114 at the proximal end thereof.

Alternatively, the opposed substantially planar end faces of the cartridge may be sealed by frangible barriers (not shown). In use, as the cartridge of the aerosol-generating article 104 is inserted into the cavity of the aerosol-generating device 106 one or more piercing members provided in the aerosol-generating device 106 may pierce the frangible barriers to allow a user to draw air though the first compartment 108 comprising the nicotine source and the second compartment 110 comprising the delivery enhancing source and out of the aerosol-generating article 104 through the mouthpiece 114 at the proximal end thereof.

As shown in FIG. 2, the single heater 118 of the aerosol-generating device 106 is received in the cavity 122 of the cartridge of the aerosol-generating article 104 when the cartridge is inserted into the cavity of the aerosol-generating device 106. The elongate electrical heating element of the single heater 118 of the aerosol-generating device 106 is thus configured as an internal heater that in use is positioned internally to the aerosol-generating article 104.

Once the cartridge of the aerosol-generating article 104 is inserted into the aerosol-generating device 106, the elongate electric heating element of the aerosol-generating device 106 heats the nicotine source in the first compartment 108 and the delivery enhancing compound source in the second compartment 110 to substantially the same temperature.

In use, the user draws on the mouthpiece 114 at the proximal and of the aerosol-generating article 104 to draw air through the first compartment 108 comprising the nicotine source and the second compartment 110 comprising the delivery enhancing compound source. As the drawn air passes through the cartridge, nicotine vapour is released from the nicotine source in the first compartment 108 and 2-(allyloxy)propanoic acid vapour is released from the delivery enhancing compound source in the second compartment 110. The nicotine vapour reacts with the 2-(allyloxy)propanoic acid vapour in the gas phase to form an aerosol of nicotine 2-(allyloxy)propanoate salt particles, which is delivered to the user through the mouthpiece 114 at the proximal end of the aerosol-generating article 104.

The invention claimed is:
1. An aerosol-generating system, comprising:
a nicotine source; and
a delivery enhancing compound source,
wherein the delivery enhancing compound source comprises a reaction product of one or both of:
(i) an alpha-keto carboxylic acid and a compound of formula (I)

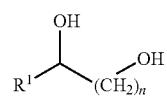

where $R^1$ is selected from alkyl, phenyl, or substituted phenyl; and
(ii) an alpha-hydroxy acid and a compound of formula (II)

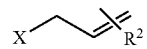

where X is a halogen and $R^2$ is selected from H, alkyl, phenyl, or substituted phenyl.

2. The aerosol-generating system according to claim 1, wherein the delivery enhancing compound source comprises the reaction product of one or both of:
(i) an alpha-keto carboxylic acid of formula (III) and a compound of formula (I)

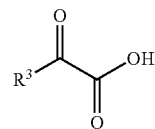

where $R^3$ is selected from $C_{1-4}$ alkyl; and
(ii) an alpha-hydroxy acid of formula (IV) and a compound of formula (II)

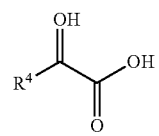

where $R^4$ is selected from $C_{1-4}$ alkyl.

3. The aerosol-generating system according to claim 1, wherein n is an integer from 1 to 4 inclusive and $R^1$ is selected from $C_{1-4}$ alkyl.

4. The aerosol-generating system according to claim 1, wherein X is Br and $R^2$ is selected from H and $C_{1-4}$ alkyl.

5. The aerosol-generating system according to claim 1, wherein the delivery enhancing compound comprises a reaction product of one or both of:
(i) pyruvic acid and the compound of formula (I); and
(ii) lactic acid and the compound of formula (II).

6. The aerosol-generating system according to claim 5, wherein the delivery enhancing compound comprises one or both of:
(i) 2,4-dimethyl-1,3-dioxolane-2-carboxylic acid; and
(ii) 2-(allyloxy)propanoic acid.

7. The aerosol-generating system according to claim 1, further comprising:
an aerosol-generating article comprising the nicotine source and the delivery enhancing compound source; and an aerosol-generating device configured to receive the aerosol-generating article.

8. The aerosol-generating system according to claim 7, wherein the aerosol-generating device comprises a heater configured to heat one or both of the nicotine source and the delivery enhancing compound source of the aerosol-generating article.

9. The aerosol-generating system according to claim 8, wherein the heater comprises a single heater configured to heat both the nicotine source and the delivery enhancing compound source of the aerosol-generating article.

10. The aerosol-generating system according to claim 7, wherein the aerosol-generating article further comprises a first compartment comprising the nicotine source and a second compartment comprising the delivery enhancing compound source.

11. The aerosol-generating system according to claim 10, wherein one or both of the first compartment and the second compartment are sealed by one or more frangible barriers, and the aerosol-generating device further comprises one or more piercing members configured to rupture the one or more frangible barriers.

12. The aerosol-generating system according to claim 10, wherein the aerosol-generating article further comprises a third compartment comprising an aerosol-modifying agent.

13. An aerosol-generating article for an aerosol-generating system, the aerosol-generating article comprising:
a nicotine source and a delivery enhancing compound source,
the aerosol-generating article being removably insertable into an aerosol-generating device,
wherein the delivery enhancing compound source comprises a reaction product of one or both of:
(i) an alpha-keto carboxylic acid and a compound of formula (I)

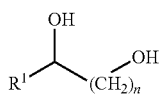
(I)

where $R^1$ is selected from alkyl, phenyl, or substituted phenyl; and
(ii) an alpha-hydroxy acid and a compound of formula (II)

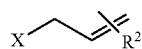
(II)

where X is a halogen and $R^2$ is selected from H, alkyl, phenyl, or substituted phenyl.

14. A method of generating an aerosol comprising nicotine salt particles, comprising:
reacting nicotine with a reaction product of one or both of:
(i) an alpha-keto carboxylic acid and a compound of formula (I)

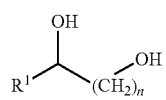
(I)

where $R^1$ is selected from alkyl, phenyl, or substituted phenyl; and
(ii) an alpha-hydroxy acid and a compound of formula (II)

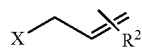
(II)

where X is a halogen and $R^2$ is selected from H, alkyl, phenyl, or substituted phenyl.

15. An aerosol-generating system for generating an aerosol comprising nicotine salt particles, comprising:
a nicotine source; and
a delivery enhancing compound source comprising one or both of:
(i) 2,4-dimethyl-1,3-dioxolane-2-carboxylic acid; and
(ii) 2-(allyloxy)propanoic acid.

* * * * *